(12) United States Patent
Lawrie

(10) Patent No.: US 9,334,327 B2
(45) Date of Patent: May 10, 2016

(54) PULMONARY HYPERTENSION

(71) Applicant: University of Sheffield, Sheffield (GB)

(72) Inventor: Allan Lawrie, Sheffield (GB)

(73) Assignee: University of Sheffield, Sheffield (GB)

( * ) Notice: Subject to any disclaimer, the term of this patent is extended or adjusted under 35 U.S.C. 154(b) by 0 days.

(21) Appl. No.: 14/352,120

(22) PCT Filed: Oct. 23, 2012

(86) PCT No.: PCT/GB2012/052629
§ 371 (c)(1),
(2) Date: Apr. 16, 2014

(87) PCT Pub. No.: WO2013/064810
PCT Pub. Date: May 10, 2013

(65) Prior Publication Data
US 2014/0255404 A1 Sep. 11, 2014

Related U.S. Application Data

(60) Provisional application No. 61/556,112, filed on Nov. 4, 2011.

(30) Foreign Application Priority Data

Nov. 1, 2011 (GB) .................................. 1118840.6

(51) Int. Cl.
| | |
|---|---|
| A61K 39/395 | (2006.01) |
| C07K 16/00 | (2006.01) |
| C07K 16/28 | (2006.01) |
| A61K 31/7105 | (2006.01) |
| A61K 31/713 | (2006.01) |
| A61K 45/06 | (2006.01) |
| C12N 15/113 | (2010.01) |
| C12Q 1/68 | (2006.01) |
| G01N 33/68 | (2006.01) |
| A61K 39/00 | (2006.01) |

(52) U.S. Cl.
CPC ........... *C07K 16/2878* (2013.01); *A61K 31/713* (2013.01); *A61K 31/7105* (2013.01); *A61K 39/3955* (2013.01); *A61K 45/06* (2013.01); *C07K 16/2875* (2013.01); *C12N 15/1138* (2013.01); *C12Q 1/6883* (2013.01); *G01N 33/6893* (2013.01); *A61K 2039/505* (2013.01); *C07K 2317/76* (2013.01)

(58) Field of Classification Search
USPC .................... 424/158.1; 435/6.11, 7.1, 7.93
See application file for complete search history.

(56) References Cited

U.S. PATENT DOCUMENTS

| | | | |
|---|---|---|---|
| 6,087,555 | A | 7/2000 | Dunstan et al. |
| 6,919,434 | B1 | 7/2005 | Goto et al. |
| 2003/0148955 | A1 * | 8/2003 | Pluenneke .................. 514/12 |
| 2003/0207827 | A1 * | 11/2003 | Boyle et al. ................. 514/44 |
| 2005/0143301 | A1 | 6/2005 | Power et al. |
| 2007/0172856 | A1 * | 7/2007 | Hogaboam ............ C07K 16/24 435/6.16 |
| 2008/0102451 | A1 * | 5/2008 | Lesniewski et al. ............. 435/6 |

FOREIGN PATENT DOCUMENTS

| | | | |
|---|---|---|---|
| WO | WO 2010/116135 A1 | 10/2010 | |
| WO | WO 2011/035433 A1 | 3/2011 | |

OTHER PUBLICATIONS

Abbas et al. Cellular and Molecular Immunology, Chapter 3, pp. 47-48; Second Edition, Copy Right 1994, 1991 by W.B. Saunders Company.*
Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495 (1994).*
Vinogradova, T et al. Osteoprotegerin expression is increased prior to haemodynamic alterations in the rat monocrotaline model of pulmonary arterial hypertension. Thorax, vol. 64, Supp. Suppl. 4, pp. A9. Abstract No. S9 (Dec. 2009).*
Miyashita et al. Osteoprotegerin (OPG) acts as an endogenous decoy receptor in tumour necrosis factor-related apoptosis-inducing ligand (TRAIL)-mediated apoptosis of fibroblast-like synovial cell. Clin Exp Immunol 137:430-436 (2004).*
Peng et al. The cross-talk between osteoclasts and osteoblasts in response to strontium treatment: Involvement of osteoprotegerin. Bone 49:1290-1298 (Available online Sep. 9, 2011).*
Accession No. PREV200700121263; Circulation; vol. 114 (18 Suppl S), pp. 130-131 (Oct. 31, 2006), Lawrie et al., "Genes Associated with Pulmonary Hypertension Regulate Osteoprotegerin in Human Pulmonary Artery Smooth Muscle Cells In Vitro," Abstract.
Accession No. PREV200800197555; Circulation; vol. 116 (16, Suppl S), pp. 123 (Oct. 16, 2007), Yu et al., "Disruption of the BMP Type II Receptor Alters the Dynamics of BMP Pathway Activation, Abrogating BMP-Mediated Grwoth Inhibition and Differentiation in Pulmonary Artery Smooth Muscle Cells," Abstract.
Accession No. PREV201000181129; Circulation; vol. 120 (18, Suppl 2), pp. SI 137 (Nov. 3, 2009), Yu et al., "Circulating Soluble Endoglin is a Sensitive Predictor of Pulmonary Arterial Hypertension and Exercise Function," Abstract.
Brun et al., "Patients with Pulmonary Hypertension Related to Congenital Systemic-to-Pulmonary Shunts are Characterized by Inflammation Involving Endothelial Cell Activation and Platelet-Mediated Inflammation," *Congenit. Heart Dis.* 4:153-159, 2009.
GB Search Report for Application No. GB1118840.6, dated Feb. 24, 2012.
Kusano, "Treatment for Pulmonary Hypertension Including Lung Transplantation," *Gen. Thorac. Cardiovasc. Surg.* 59:538-546, 2011.

(Continued)

*Primary Examiner* — Elizabeth C Kemmerer
*Assistant Examiner* — Regina M Deberry
(74) *Attorney, Agent, or Firm* — Klarquist Sparkman, LLP

(57) ABSTRACT

The disclosure relates to agents that inhibit the activity of osteoprotegerin and their use in the treatment of pulmonary hypertension.

11 Claims, 9 Drawing Sheets

(56) References Cited

OTHER PUBLICATIONS

Lawrie et al., "Evidence of a Role for Osteoprotegerin in the Pathogenesis of Pulmonary Arterial Hypertension," *Am. J. Pathol.* 172:256-264, 2008.

Lawrie et al., "Paigen Diet-Fed Apolipoprotein E Knockout Mice Develop Severe Pulmonary Hypertension in an Interleukin-1-Dependent Manner," *Am. J. Pathol.* 179:1693-1705, 2011.

Lawrie et al., "Osteoprotegerin Blockade Prevents and Reverses Experimental Pulmonary Arterial Hypertension," *Am. J. Respir. Crit. Care Med.* 185:A6515, 2012.

Sultan et al., "Osteoprotegerin, Thiazolidinediones Treatment, and Silent Myocardial Ischemia in Type 2 Diabetic Patients," *Diabetes Care* 31:593-595, 2008.

Watt et al. "OPG:TRAIL Ratio as a Potential Biomarker for Pulmonary Arterial Hypertension" 82nd Scientific Session of the American-Heart-Association; Orlando, FL, USA; Nov. 14-18, 2009. *Circulation* vol. 120, No. 18, Suppl 2, p. S806, Nov. 3, 2009. Accession No. PREV201000179758, Database Biosis, 2009.

Bennett et al., Osteoprotegerin Inactivation Accelerates Advanced Atherosclerotic Lesion Progression and Calcification in Older ApoE$^{-/-}$ Mice (*Arterioscler Thromb Vasc Biol.* 26:2117-2124, 2006.

Ovchinnikova et al., "Osteoprotegerin Promotes Fibrous Cap Formation in Atherosclerotic Lesions of ApoE-Deficient Mice—Brief Report," *Arterioscler Thromb Vasc Biol.* 29:1478-1480, 2009.

Papadopouli et al., "Role of OPG/RANKL/RANK axis on the vasculature," *Histol Histopathol.* 23:497-506, 2008.

Riches et al., "Osteoporosis Associated with Neutralizing Autoantibodies against Osteoprotegerin," *N Engl J Med.* 361:1459-1465, 2009.

Sasaki et al., "Glucocorticoid Decreases Circulating Osteoprotegerin (OPG): Possible Mechanism for Glucocorticoid Induced Osteoporosis," *Nephrol Dial Transplant.* 16:479-482, 2001.

Van Campenhout and Golledge, "Osteoprotegerin, Vascular Calcification and Atherosclerosis," *Atherosclerosis* 204:321-329, 2009.

\* cited by examiner

FIG. 2

SEQ ID NO: 1

MNNLLCCALVFLDISIKWTTQETFPPKYLHYDEETSHQLLCDKCPPGTYLKQHCTAKWKT
VCAPCPDHYYTDSWHTSDECLYCSPVCKELQYVKQECNRTHNRVCECKEGRYLEIEFCLK
HRSCPPGFGVVQAGTPERNTVCKRCPDGFFSNETSSKAPCRKHTNCSVFGLLLTQKGNAT
HDNICSGNSESTQKCGIDVTLCEEAFFRFAVPTKFTPNWLSVLVDNLPGTKVNAESVERI
KRQHSSQEQTFQLLKLWKHQNKDQDIVKKIIQDIDLCENSVQRHIGHANLTFEQLRSLME
SLPGKKVGAEDIEKTIKACKPSDQILKLLSLWRIKNGDQDTLKGLMHALKHSKTYHFPKT
VTQSLKKTIRFLHSFTMYKLYQKLFLEMIGNQVQSVKISCL

SEQ ID NO: 2

<u>ATGAACAACTTGCTGTGCTGCGCGCTCGTGTTTCTGGACATCTCCATTAAGTGGACCACC</u>

<u>CAGGAAACG</u>TTTCCTCCAAAGTACCTTCATTATGACGAAGAAACCTCTCATCAGCTGTTG

TGTGACAAATGTCCTCCTGGTACCTACCTAAAACAACACTGTACAGCAAAGTGGAAGACC

GTGTGCGCCCCTTGCCCTGACCACTACTACACAGACAGCTGGCACACCAGTGACGAGTGT

CTATACTGCAGCCCCGTGTGCAAGGAGCTGCAGTACGTCAAGCAGGAGTGCAATCGCACC

CACAACCGCGTGTGCGAATGCAAGGAAGGGCGCTACCTTGAGATAGAGTTCTGCTTGAAA

CATAGGAGCTGCCCTCCTGGATTTGGAGTGGTGCAAGCTGGAACCCCAGAGCGAAATACA

GTTTGCAAAAGATGTCCAGATGGGTTCTTCTCAAATGAGACGTCATCTAAAGCACCCTGT

AGAAAACACACAAATTGCAGTGTCTTTGGTCTCCTGCTAACTCAGAAAGGAAATGCAACA

CACGACAACATATGTTCCGGAAACAGTGAATCAACTCAAAAATGTGGAATAGATGTTACC

CTGTGTGAGGAGGCATTCTTCAGGTTTGCTGTTCCTACAAAGTTTACGCCTAACTGGCTT

AGTGTCTTGGTAGACAATTTGCCTGGCACCAAAGTAAACGCAGAGAGTGTAGAGAGGATA

AAACGGCAACACAGCTCACAAGAACAGACTTTCCAGCTGCTGAAGTTATGGAAACATCAA

AACAAAGACCAAGATATAGTCAAGAAGATCATCCAAGATATTGACCTCTGTGAAAACAGC

GTGCAGCGGCACATTGGACATGCTAACCTCACCTTCGAGCAGCTTCGTAGCTTGATGGAA

AGCTTACCGGGAAAGAAAGTGGGAGCAGAAGACATTGAAAAAACAATAAAGGCATGCAAA

CCCAGTGACCAGATCCTGAAGCTGCTCAGTTTGTGGCGAATAAAAAATGGCGACCAAGAC

ACCTTGAAGGGCCTAATGCACGCACTAAAGCACTCAAAGACGTACCACTTTCCCAAAACT

GTCACTCAGAGTCTAAAGAAGACCATCAGGTTCCTTCACAGCTTCACAATGTACAAATTG

TATCAGAAGTTATTTTTAGAAATGATAGGTAACCAGGTCCAATCAGTAAAAATAAGCTGC

TTATAA

PULMONARY HYPERTENSION

CROSS REFERENCE TO RELATED APPLICATIONS

This is the U.S. National Stage of International Application No. PCT/GB2012/052629, filed Oct. 23, 2012, which was published in English under PCT Article 21(2), which in turn claims the benefit of Great Britain Application No. 1118840.6, filed Nov. 1, 2011, and U.S. Provisional Application No. 61/556,112, filed Nov. 4, 2011. The provisional application is incorporated herein in its entirety.

FIELD OF THE INVENTION

The disclosure relates to agents that inhibit the activity of osteoprotegerin (OPG) and their use in the treatment of pulmonary hypertension.

BACKGROUND TO THE INVENTION

Pulmonary Hypertension [PH] covers a variety of conditions that result in abnormally high blood pressure in the lungs. PH can be in the form of pulmonary arterial hypertension (PAH) occurring in either its idiopathic (IPAH) or hereditary (hPAH) and also in association with other diseases (APAH) e.g. connective tissue disease. PH can also result from left heart disease, lung diseases (particularly Congestive Obstructive Disease [COPD] and pulmonary fibrosis), thrombo-embolism as well as may other multifactorial conditions such as portal hypertension, sickle cell disease and HIV. The prognosis for patients suffering from PH is poor and varies between disease groups. Current management of the disease includes the use of calcium channel blockers, diuretics, enthothelin receptor antagonists, prostacyclins, soluble guanalate cyclase and phosphodiesterase inhibitors. The side effect profiles of these treatments can result in further reduced quality of life and unsatisfactory disease control. In lung transplantation is the only curative treatment but is very rarely done. Therefore there is a continuing need to identify new treatments and agents that are effective at slowing progression and/or reversing PH and which do not have the problems associated with current treatments.

Osteoprotegerin (OPG) is a protein of the Tumour Necrosis Factor (TNF) receptor family and binds at least two ligands; TNF-related apoptosis inducing ligand [TRAIL] which is a TNF-like cell surface molecule involved in the induction of apoptosis in cancer cells and Receptor activator of NFkB ligand [RANKL] which is expressed on osteoclast precursors, dendritic cells, T-cells and haematopoietic precursors. OPG is seen as one of a number of decoy receptors for TRAIL, acting to modulate its ability to target cancer cells. OPG might be expected to enhance cancer cell survival if present at a relevant site and its ability to increase the survival of tumour cells has been documented. RANKL interacts with RANK on cell surfaces to stimulate the production and activity of osteoclasts, the principal cells involved in bone turnover. The interaction of OPG with RANKL inhibits RANKL's ability to bind to RANK and stimulate osteoclasts and it is this activity of OPG that confers its ability to reduce bone loss.

The activity of OPG in bone metabolism is well known in the art. U.S. Pat. No. 6,015,938 discloses a transgenic non-human animal that expresses OPG and its use in analysing the involvement of OPG in bone metabolism. U.S. Pat. No. 6,284,740 discloses a gene therapy method for increasing the amount of OPG produced by a mammal thereby increasing bone density. U.S. Pat. Nos. 6,284,728 and 6,613,544 disclose and claims an OPG polypeptide and a nucleic acid molecule that encodes OPG respectively. U.S. Pat. No. 6,316, 408 discloses a method to treat or prevent a bone disease by administration of an osteoclast activation and differentiation factor Transgenic mice lacking expression of OPG are described in U.S. Pat. No. 6,087,555. In all cases OPG and its involvement in bone metabolism is taught. In none of the prior art cited is the involvement of OPG in PH suggested or the beneficial effects of blocking OPG activity and its therapeutic effect on PH development.

This disclosure relates to the use of OPG antagonists in the treatment of PH. We illustrate this using antagonistic antibodies directed to OPG and show that blocking OPG activity protects animals that have a predisposition to PH and the reversal of pathological symptoms.

STATEMENTS OF INVENTION

According to an aspect of the invention there is provided an agent that inhibits the expression of osteoprotegerin [OPG] or the activity of a protein encoded by the OPG gene for use in the treatment of pulmonary hypertension.

In a preferred embodiment of the invention said inhibitor is an antagonistic antibody, or active binding fragment thereof.

In a preferred embodiment of the invention said antibody or binding fragment binds and inhibits the activity of a polypeptide comprising or consisting of the amino acid sequence in SEQ ID NO: 1, or an antigen binding part or a sequence variant that has between 75%-99% sequence identity with the amino acid sequence in SEQ ID NO: 1.

A sequence variant is a functionally equivalent polypeptide of SEQ ID NO: 1 and one in which one or more amino acid residues are substituted with conserved or non-conserved amino acid residues, or one in which one or more amino acid residues includes a substituent group. Conservative substitutions are the replacements, one for another, among the aliphatic amino acids Ala, Val, Leu and Ile; interchange of the hydroxyl residues Ser and Thr; exchange of the acidic residues Asp and Glu; substitution between amide residues Asn and Gln; exchange of the basic residues Lys and Arg; and replacements among aromatic residues Phe and Tyr.

In addition, the invention features polypeptide sequences having at least 75% identity with the polypeptide sequences illustrated in SEQ ID NO: 1, or fragments and antigenic polypeptides thereof. In one embodiment, the polypeptides have at least 85% identity, more preferably at least 90% identity, even more preferably at least 95% identity, still more preferably at least 97% identity, and most preferably at least 99% identity with the amino acid sequences illustrated in SEQ ID NO: 1.

In a preferred embodiment of the invention said antibody competes with an antibody that binds to the amino acid sequence as represented in SEQ ID NO: 1.

In a preferred embodiment of the invention said antibody is a polyclonal antibody.

In an alternative preferred embodiment of the invention said antibody is a monoclonal antibody.

Antibodies, also known as immunoglobulins, are protein molecules which have specificity for foreign molecules (antigens). Immunoglobulins (Ig) are a class of structurally related proteins consisting of two pairs of polypeptide chains, one pair of light (L) (low molecular weight) chain (κ or λ), and one pair of heavy (H) chains (γ, α, μ, δ and ε), all four linked together by disulphide bonds. Both H and L chains have regions that contribute to the binding of antigen and that are highly variable from one Ig molecule to another. In addition, H and L chains contain regions that are non-variable or constant. The L chains consist of two domains. The carboxy-terminal domain is essentially identical among L chains of a given type and is referred to as the "constant" (C) region. The amino terminal domain varies from L chain to L chain and contributes to the binding site of the antibody. Because of its variability, it is referred to as the "variable" (V) region. The H chains of Ig molecules are of several classes, α, μ, σ, α, and γ (of which there are several sub-classes). An assembled Ig molecule consisting of one or more units of two identical H and L chains, derives its name from the H chain that it possesses. Thus, there are five Ig isotypes: IgA, IgM, IgD, IgE and IgG (with four sub-classes based on the differences in the H chains, i.e., IgG1, IgG2, IgG3 and IgG4). Further detail regarding antibody structure and their various functions can be found in, Using Antibodies: A laboratory manual, Cold Spring Harbour Laboratory Press.

In a preferred embodiment of the invention said fragment is a single chain antibody fragment.

Various fragments of antibodies are known in the art, e.g. Fab, $Fab_2$, $F(ab')_2$, Fv, Fc, Fd, etc. A Fab fragment is a multimeric protein consisting of the immunologically active portions of an immunoglobulin heavy chain variable region and an immunoglobulin light chain variable region, covalently coupled together and capable of specifically binding to an antigen. Fab fragments are generated via proteolytic cleavage (with, for example, papain) of an intact immunoglobulin molecule. A $Fab_2$ fragment comprises two joined Fab fragments. When these two fragments are joined by the immunoglobulin hinge region, a $F(ab')_2$ fragment results. An Fv fragment is a multimeric protein consisting of the immunologically active portions of an immunoglobulin heavy chain variable region and an immunoglobulin light chain variable region covalently coupled together and capable of specifically binding to an antigen. A fragment could also be a single chain polypeptide containing only one light chain variable region, or a fragment thereof that contains the three CDRs of the light chain variable region, without an associated heavy chain variable region, or a fragment thereof containing the three CDRs of the heavy chain variable region, without an associated light chain moiety; and multi specific antibodies formed from antibody fragments, this has for example been described in U.S. Pat. No. 6,248,516.

Fv fragments or single region (domain) fragments are typically generated by expression in host cell lines of the relevant identified regions. These and other immunoglobulin or antibody fragments are within the scope of the invention and are described in standard immunology textbooks such as Paul, *Fundamental Immunology* or Janeway's Immunobiology, Murphy, K., Travers, P. & Walport P.

Molecular biology now allows direct synthesis (via expression in cells or chemically) of these fragments, as well as synthesis of combinations thereof. A fragment of an antibody or immunoglobulin can also have bispecific function as described above.

In a preferred embodiment of the invention said antibody is a chimeric antibody.

In an alternative preferred embodiment of the invention said antibody is a humanized or human antibody.

Chimeric antibodies are recombinant antibodies in which all of the V-regions of a mouse or rat antibody are combined with human antibody C-regions. Humanised antibodies are recombinant hybrid antibodies which fuse the complementarity determining regions from a rodent antibody V-region with the framework regions from the human antibody V-regions. The C-regions from the human antibody are also used. The complementarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanised antibodies have reduced antigenicity when injected to a human subject because there is a reduced amount of rodent (i.e. foreign) antibody within the recombinant hybrid antibody, while the human antibody regions do not elicit an immune response. This results in a weaker immune response and a decrease in the clearance of the antibody. This is clearly desirable when using therapeutic antibodies in the treatment of human diseases. Humanised antibodies are designed to have less "foreign" antibody regions and are therefore thought to be less immunogenic than chimeric antibodies.

In a preferred embodiment of the invention said antibody or binding fragment binds the ligand binding domain of OPG.

In an alternative preferred embodiment of the invention said agent is an antisense oligonucleotide.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and thereby, inhibits the transcription of that gene and/or the translation of that mRNA. The antisense molecules are designed so as to interfere with transcription or translation of a target gene upon hybridization with the target gene. Those skilled in the art will recognize that the exact length of the antisense oligonucleotide and its degree of complementarity with its target will depend upon the specific target selected, including the sequence of the target and the particular bases which comprise that sequence.

In a preferred embodiment of the invention said antisense oligonucleotide is an antisense RNA molecule and is part of a siRNA or shRNA molecule.

A technique to specifically ablate gene function is through the introduction of double stranded RNA, also referred to as small inhibitory or interfering RNA (siRNA), into a cell which results in the destruction of m RNA complementary to the sequence included in the siRNA molecule. The siRNA molecule comprises two complementary strands of RNA (a sense strand and an antisense strand) annealed to each other to form a double stranded RNA molecule. The siRNA molecule is typically derived from exons of the gene which is to be ablated. The mechanism of RNA interference is being elucidated. Many organisms respond to the presence of double stranded RNA by activating a cascade that leads to the formation of siRNA. The presence of double stranded RNA activates a protein complex comprising RNase III which processes the double stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the m RNA.

In a preferred embodiment of the invention said antisense oligonucleotide or antisense RNA is 19-29 nucleotides [nt] in length; preferably 21 nt in length.

In a preferred embodiment of the invention said antisense olignucleotide, siRNA or shRNA molecule includes modified nucleotides.

The term "modified" as used herein describes a nucleic acid molecule in which;
i) at least two of its nucleotides are covalently linked via a synthetic internucleoside linkage (i.e., a linkage other than a phosphodiester linkage between the 5' end of one nucleotide and the 3' end of another nucleotide). Alternatively or preferably said linkage may be the 5' end of one nucleotide linked to the 5' end of another nucleotide or the 3' end of one nucleotide with the 3' end of another nucleotide; and/or
ii) a chemical group, such as cholesterol, not normally associated with nucleic acids has been covalently attached to the double stranded nucleic acid.
iii) Preferred synthetic internucleoside linkages are phosphorothioates, alkylphosphonates, phosphorodithioates, phosphate esters, alkylphosphonothioates, phosphoramidates, carbamates, phosphate triesters, acetamidates, peptides, and carboxymethyl esters.

The term "modified" also encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2; azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4,N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5 carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2 methylthio-N6-isopentenyladenine; uracil-5-oxyacetic acid methyl ester; pseudouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpseudouracil; 1-methylguanine; 1-methylcytosine. Modified double stranded nucleic acids also can include base analogs such as C-5 propyne modified bases (see Wagner et al., Nature Biotechnology 14:840-844, 1996).

Preferably said antisense oligonucleotide, siRNA or shRNA molecule comprises a nucleotide sequence designed with reference to SEQ ID NO: 2.

In a preferred embodiment of the invention said agent is combined with a carrier adapted to deliver said antisense oligonucleotide, siRNA or shRNA molecule to a cell or tissue.

The delivery of antisense oligonucleotide, siRNA or shRNA is achieved using delivery vehicles known in the art. For example siRNA can be chemically modified and conjugated to a lipophilic cholesterol moiety at the 3' end of the sense strand. Cationic delivery systems can also be employed in the delivery of siRNA. These include cationic lipids and liposomes, cationic polymers, cationic dendrimers and cationic cell penetrating peptides. The cationic delivery vehicles have a common positive charge which facilitates complex formation with negatively charged siRNA. Commercially available examples of liposome based delivery vehicles include Lipofectin, RNAifect, Oligofectamine, Lipofectamine and TransIT TKO have been used in vitro. DOTAP (N [1-(2,3-dioleoyloxy)]-N,N,N-trimethyl ammonium propane) and Oligfectamine have been utilised in vivo. Other liposome based delivery vehicle includes solid nucleic acid lipid particles [SNALPs] which are also conjugated with polyethylene glycol. Peptide delivery vehicles have also been successful in delivering siRNA. Pegylated polyethyleneimine [PEI] comprising RGD peptides have been used to target siRNA to angiogenesis factors such as VEGF. Atelocollagen has been used in the delivery of siRNA to tumours in vivo. Delivery of siRNA has also been demonstrated using cyclodextrin polymers. A yet further example of a siRNA delivery vehicle are self assembled LPD nanoparticles which have been used to deliver to solid and metastatic tumours. LPD nanoparticles comprise cationic lipids combined with protamine which interacts with negatively charged siRNA. Pegylated versions of LPD nanoparticles are also known which have improved pharmacokinetics. Reviews of current delivery vehicles can be found in Molecular Pharmaceutics 2008 Vol 6[3] p 651-658; The AAPS Journal 2009 Vol 11 [4] p 639; Pharmaceutical Research 2009, Vol 26[3] p 657; and Nature Reviews 2009 Vol 8, p 129.

When administered the agents of the present invention are administered in pharmaceutically acceptable preparations. Such preparations may routinely contain pharmaceutically acceptable concentrations of salt, buffering agents, preservatives, compatible carriers and supplementary anti-cancer agents.

The agents of the invention can be administered by any conventional route, including injection or by gradual infusion over time. The administration may, for example, intravenous, intraperitoneal, intramuscular, intracavity, subcutaneous, transdermal or trans-epithelial.

The agents of the invention are administered in effective amounts. An "effective amount" is that amount of an agent that alone, or together with further doses, produces the desired response. In the case of treating pulmonary hypertension, the desired response is inhibiting the progression of the disease. This may involve only slowing the progression of the disease temporarily, although more preferably, it involves halting the progression of the disease permanently. This can be monitored by routine methods. Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The agents used in the foregoing methods preferably are sterile and contain an effective amount of an agent according to the invention for producing the desired response in a unit of weight or volume suitable for administration to a patient.

The doses of agents according to the invention administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, doses of antisense oligonucleotide, siRNA or shRNA of between 1 nM-1 µM generally will be formulated and administered according to standard procedures. Preferably doses can range from 1 nM-500 nM, 5 nM-200 nM, and 10 nM-100 nM. Other protocols for the administration of compositions will be known to one of ordinary skill in the art, in which the dose amount, schedule of injections, sites of injections, mode of administration and the like vary from the foregoing. The administration of compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep, goat, dog, cat or rodent.

When administered, the agent preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents' (e.g. those typically used in the treatment of pulmonary hypertension). When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Agents may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" in this context denotes an organic or inorganic ingredient, natural or synthetic, with which the active ingredient is combined to facilitate the application, (e.g. liposome or immuno-liposome). The components of the pharmaceutical compositions also are capable of being co-mingled with the agents of the present invention, and with each other, in a manner such that there is no interaction which would substantially impair the desired pharmaceutical efficacy.

The pharmaceutical compositions containing agents according to the invention may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal.

The agents may conveniently be presented in unit dosage form and may be prepared by any of the methods well-known in the art of pharmacy. All methods include the step of bringing the active agent into association with a carrier which constitutes one or more accessory ingredients. Compositions containing agents according to the invention may be administered as aerosols and inhaled. Compositions suitable for parenteral administration conveniently comprise a sterile aqueous or non-aqueous preparation of agent, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

In a preferred embodiment of the invention said composition includes an effective amount of at least one additional agent effective in the treatment of pulmonary hypertension.

In a preferred embodiment of the invention said agent is selected from the group: calcium channel blockers, diuretics, endothelin receptor antagonists, prostacyclins, soluble guanalate cyclase and phosphodiesterase inhibitors.

In a preferred embodiment of the invention pulmonary hypertension is selected from the group consisting of: pulmonary arterial hypertension and PH associated with lung disease.

According to a further aspect of the invention there is provided a method to treat pulmonary hypertension comprising administering an effective amount of an osteoprotegerin antagonist to a human subject in need of treatment.

According to a further aspect of the invention there is provided a diagnostic or prognostic method for determining if a subject has or has a predisposition to pulmonary hypertension comprising determining the expression of OPG wherein over-expression of OPG when compared to a control sample is indicative of pulmonary hypertension or a predisposition to pulmonary hypertension.

In a preferred method of the invention said method comprises:
  i) providing an isolated biological sample to be tested;
  ii) forming a preparation comprising said sample and an oligonucleotide primer pair adapted to anneal to a nucleic acid molecule comprising a nucleic acid sequence as represented in SEQ ID NO: 2; a thermostable DNA polymerase, deoxynucleotide triphosphates and co-factors;
  iii) providing polymerase chain reaction conditions sufficient to amplify said nucleic acid molecule;
  iv) analysing the amplified products of said polymerase chain reaction for the presence or absence of a nucleic acid molecule comprising a nucleotide sequence derived from SEQ ID NO: 2 and optionally
  v) comparing the amplified product with a normal matched control.

In an alternative preferred method of the invention said method comprises:
i) providing an isolated biological sample to be tested;
ii) forming a preparation comprising said sample and an antibody or antibodies that specifically binds one or more polypeptide[s] in said sample as represented by the amino acid sequences presented in SEQ ID NO: 1 to form an antibody/polypeptide complex;
iii) detecting the complex or complexes so formed; and
iv) comparing the expression of said polypeptide[s] with a normal matched control.

In a preferred method of the invention the expression of OPG is compared to the expression of TRAIL in said sample.

In a preferred method of the invention ratio of OPG:TRAIL is compared to the ratio of OPG:TRAIL in a control sample.

In a further preferred embodiment of the invention said method includes the administration of an effective amount of an OPG antibody as hereindisclosed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE FIGURES

An embodiment of the invention will now be described by example only and with reference to the following figures.

MATERIALS AND METHODS

Figure 1A:
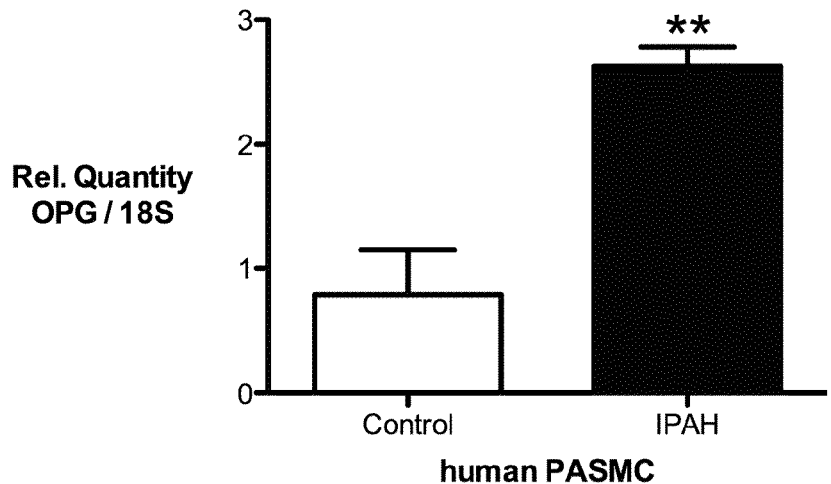
FIG. 1 A) OPG mRNA is significantly increased in pulmonary artery smooth muscle cells (PASMC) isolated from patients with idiopathic pulmonary arterial hypertension (IPAH) compared to those isolated from control lung; B) OPG protein is significantly elevated in the serum of patients with IPAH compared to age matched controls; C) OPG secretion from human PASMCs is stimulated by the addition of serotonin (5-HT); D) OPG secretion from human PASMCs is stimulated by the knock-down of BMP-R2 by BMP-R2 siRNA (BMP-R2 si); E) OPG secretion from human PASMCs is stimulated by addition of recombinant Il-1 beta; F) Recombinant human OPG (rOPG) induces of human PASMC proliferation as shown by the incorporation of tritiated thymidine in a dose dependant manner; G) rOPG induces the migration of human PASMCs in a dose-dependant manner; H) Haemodynamic changes consistent with PAH result in a significant elevation in right ventricular systolic pressure (RVSP) in rats treated with monocrotaline (Mct) from 21 days after subcutaneous injection compared to saline treated control rats; I) Pulmonary vascular remodelling that drives the haemodynamic alterations in the rat Mct model become apparent as early as 7 days after the initiation of disease; J) Serum levels of OPG are significantly elevated in the rat Mct model from 14 days, prior to significant increases in RVSP; K) OPG gene expression in total lung lysates is significantly elevated at 21 days post Mct treatment; L) Total lung protein expression of OPG is significantly elevated from 21 days post monocrotaline (Mct) injection compared to saline treated control rats; M) Rats treated with an anti-OPG antibody delivered by a subcutaneous osmotic pump were protected from developing PAH in response to monocrotaline. In contrast rats receiving IgG developed significantly elevated RVSP; N) As M) showing the significant increase in small <50 μm pulmonary artery/arteriole remodelling (as shown by media/cross-sectional area (media/CSA) in IgG treated rats compared to those treated with the anti-OPG antibody; O) As N) showing the significant increase in small to mid-sized (51-100 μm) pulmonary artery muscularisation as expressed by medial area/cross sectional area (Media/CSA) in the IgG treated rats compared to those treated with the anti-OPG antibody; P) ApoE−/− and ApoE−/−/IL-1R1−/− mice develop severe PAH in response to feeding of the Paigen diet for 8 weeks; Q) OPG gene expression in total lung lysates is significantly elevated Paigen diet fed ApoE−/− and ApoE−/−/IL-1R1−/− mice with severe PAH compared to chow-fed littermates; R) OPG protein in total lung lysates is significantly elevated Paigen diet fed ApoE−/− and ApoE−/−/IL-1R1−/− mice with severe PAH compared to chow-fed littermates; S) Treatment of established PAH in the Paigen-fed ApoE−/− model with a subcutaneous osmotic pump delivering an anti-OPG antibody for 4 weeks from week 8 of the procedure resulted a reduction of RVSP down to near normal levels compared to mice treated with IgG in which the disease progressed further; T) Treatment of established PAH in the Paigen-fed ApoE−/−/IL-1R1−/− model with a subcutaneous osmotic pump delivering an anti-OPG antibody for 4 weeks from week 8 of the procedure resulted a reduction of RVSP down to near normal levels compared to mice treated with IgG in which the disease progressed further; U) Treatment of ApoE (−/−) mice with anti-OPG antibody showed disease reversal. The disease reversal and normalisation of haemodynamics was associated with a significant reduction in the Degree of pulmonary vascular remodelling (Media/CSA) due to a significant reduction in proliferating cells (PCNA positive) and significant increase in apoptosis (TUNEL positive); V) ApoE/OPG (−/−) mice show that these mice are protected from developing pulmonary Hypertension FIG. 2 provides a protein (SEQ ID NO: 1) and coding sequence (SEQ ID NO: 2) of OPG.

Animals
Rats

Outbred male, albino Sprague Dawley rats (Charles River or Harlan, U.K) (starting weight approx. 200 g) were used for experiments. A single subcutaneous injection of monocrotaline (MCT) (Sigma Aldrich, UK) into the left thigh was used to induce pulmonary arterial hypertension. We used a well established dose of 60 mg/kg that leads to the development of severe PAH which is fatal within 5-6 weeks.

200 mg of Monocrotaline (MCT) was first fully dissolved in 0.6 ml of 1M Hydrochloric Acid and vortexed for 40 min. Sterile water was added to make the volume to 5 ml and the pH adjusted to 7.0 with sterile NaOH. A final solution to 10 ml was made with sterile water.

Mice

All inbred mice were on a C57BL/6 background and deficient for Apolipoprotein-E (ApoE−/−). Mice were available from in house colonies at the University of Sheffield. ApoE−/− (Jax 2052) mice were originally sourced from Jackson laboratories (Bar Habor, Me., USA). Male mice aged between 8-14 weeks were used for all in vivo experiments. OPG$^{-/-}$ mice were obtained from JAX labs, USA (B6.12954-

Tnfrsf11b<tm1Eac>/J, stock number 010672) and subsequently crossed through 7 generations with ApoE$^{-/-}$ (Jax 2052) originally sourced from Jackson laboratories to generate the ApoE$^{-/-}$/OPG$^{-/-}$ mice.

Diets and Husbandry

Rodents were fed standard laboratory chow (4.3% fat, 0.02% cholesterol, and 0.28% sodium, Harlan, UK). Where indicated experimental mice were fed a high fat atherogenic diet (referred to here on as Paigen) which consisted of 18.5% fat, 0.9% cholesterol, 0.5% cholate, and 0.259% sodium for either 8 or 12 weeks (special Diet services, UK). All animals had access to drinking water and fed ad-libitum. They were housed in dedicated laboratories with controlled temperature, humidity and a 12 h day-night cycle.

Animal care and investigation conformed to the University's ethical policy statement and the UK Home office guidance in the operation of Animal Scientific Procedures Act 1986. AH was in a receipt of a UK home office personal license (PIL 40/9332) and worked with procedures detailed in a H.O project license held by AL (PPL 40/2952).

Interventions

Where stated polyclonal goat anti-mouse OPG (Anti-OPG) or control goat IgG isotype antibodies (R&D systems, UK) where delivered to rodents through subcutaneously implanted osmotic pumps (Durect Corp., CA, USA). Interventions were delivered via an Alzet® 1004 micro pump (100 µl reservoir, 0.1 µl/hour for 4 weeks) in mice and via an Alzet® 2002 mini-pump (200 µl reservoir, 0.5 µl/hr, 85 ng/hr for 2 weeks) in rats.

Pump Implantation Protocol

Each pump was filled with the appropriate intervention under sterile conditions in a class II laminar flow hood and placed in sterile 0.9% saline at 37° C. 24 hours prior to implantation. Under isoflurane gas anaesthesia (2-3%, Iso-Flo® 100% w/w inhalation vapour liquid, Abbot laboratories Ltd, Kent, UK) through 100% oxygen (flow rate 1.5 L/min) overlying fur was clipped, the skin cleaned and sterilised prior to making a 1-1.5 cm cutaneous incision over the left posterolateral thoracic wall, inferior to the lower costal margin. Under sterile surgical conditions, pre-filled pumps were implanted into a subcutaneous pocket created with blunt dissection. The wound was subsequently cleaned and closed using interrupted 2-0 Vicryl absorbable sutures (B-Braun, Sheffield, UK). Implantation for mice was identical except pumps were primed for 48 hours, implanted posterior to the cervical spine (scruff line) and wounds closed with interrupted Silk sutures (Silkam®, B-Braun Sheffield, UK).

Experimental Protocol

Mice

ApoE−/− knockout mice (10-16 weeks of age, n=4-7/group) where fed either chow or Paigen for 8 weeks before disease phenotyping (see below).

To determine the efficacy of inhibiting OPG in mice with established disease, ApoE−/− mice (8-10 weeks of age, n=6-7/group) were fed a Paigen diet for 8 weeks and then received an anti-OPG antibody (20 ng/hr) or isotype control with phenotyping performed at week 12.

Rats

In time course experiments rats (200-260 g, n=7/group/time-point) underwent haemodynamic study and sacrifice either 2, 7, 14, 21 or 28 days after injection with MCT (60 mg/kg) or saline control.

To investigate if OPG was required for the development of disease (Prevention study) rats (200-240 g, n=4/group) were treated with an anti-OPG antibody (84 ng/hr) or isotype control delivered for 2 weeks by osmotic pumps, commencing at baseline with MCT injection. Disease phenotyping was undertaken one week later, i.e.: 21 days after MCT injection.

Disease Phenotyping

Each rodent underwent echocardiography (where indicated) before cardiac catheterisation and was then sacrificed whilst still under anaesthesia. Blood was collected by cardiac puncture for serum and isolation of RNA (where indicated). The abdominal aorta was cut and lungs were perfused with PBS via a needle in the right ventricle until the lungs became visibly white. The heart and lungs were removed en-bloc. The right lung was quickly separated before immediately being snap frozen in liquid nitrogen for subsequent biochemical analyses. The left lung was perfusion fixed, via the trachea with 10% (v/v) formalin at an inflation pressure of 20 cm $H_2O$ and then placed with the heart in 10% formalin overnight at 40 C. The left lung was subsequently used for histological and immunohistochemical analyses.

Rodent Echocardiography

Transthoracic echocardiography was performed with a preclinical high frequency ultrasound imaging system (Vevo 770®, Visual Sonics, Toronto, Canada) using either a RMV707B (mouse) or RMV710B (rat) scan head. Rodents were anaesthetised with isoflurane via oxygen before being placed supine on a heated platform and covered to minimise heat loss. Maintenance Isoflurane (0.5-1.5%) with oxygen was delivered via a nose cone and adjusted to achieve maximal heart rate (approx. 500 bpm for mice and 350 bpm for rats) which was continuously recorded along with respiration rate and rectal temperature. The chest of the mouse was depilated and preheated ultrasound gel was applied (Aquasonics 100 Gel, Parker Labs Inc. New Jersey, U.S) for subsequent image acquisition.

Study Protocol

Left Ventricle: Standard parameters of the left ventricle were measured in the short axis view at the mid-papillary muscle level. Manual tracing of the LV end diastolic and systolic areas were made to derive the fractional area change (FAC) as the primary index of contractility. M-Mode measurements were made for the LV wall and cavity dimensions (LVIDd), from which the ejection fraction (EF %), fractional shortening (FS %) and corrected LV mass were determined by standard automated analysis. Pulse wave tissue doppler (TDI) velocities were manually recorded from the endocardial aspect of the posterior wall of the left ventricle and represented another independent index of contractility. Stroke volume was derived from measuring the Velocity Timed integral (VTi) of flow and diameter at the level of aortic valve annulus and multiplied by heart rate to obtain the cardiac output.

Right Ventricle and Pulmonary Artery: From the right parasternal long axis view, right ventricle free wall measurements were recorded with M-Mode function. From the short axis view, doppler flow was recorded from the proximal pulmonary artery (just after the pulmonary valve). From the spectral Doppler tracing the time from onset of flow to peak velocity (PA acceleration time; PAAT), the duration of ejection (PA ejection time; PAET) and stroke work (PA VTI) were measured.

Analysis was performed offline using the accompanying software (Vevo 770, V3.0). Measurements were taken during the relevant phase of the cardiac cycle that did not coincide with inspiration artefact. To minimise inter-observer variability all image acquisition and analyses were performed by a single, experienced operator (AGH) blind to the status experimental subjects.

Cardiac Catheterisation

Following echocardiography, right and left (where indicated) ventricular catheterisation was performed using a closed chest method via the right external jugular vein and right internal carotid artery. Data were acquired with pre-soaked Millar high fidelity micromanometer catheters. (For mice 1Fr SPR-1000 pressure/1 Fr PVR-1045 pressure volume catheters and in rats 2Fr SPR-320 pressure/SPR-838 pressure volume catheters were used, Millar instruments, Houston, Tex., USA). The catheters were connected to a Millar MPVS 300 and a PowerLab 8/30 data acquisition system (AD Instruments, Oxfordshire, UK) and recorded using Chart v6 and v7 software (AD Instruments). Pressure tracings were recorded when tracings had stabilized and reached a steady state. Right Ventricular Systolic Pressure (RVSP) was used to define pulmonary hypertension and is equivalent to the Pulmonary Artery Systolic Pressure (PASP) in the absence an obstruction between the right ventricle and pulmonary artery. Where indicated pressure volume analysis was performed using PVAN v2.3.

Protocol for Vascular Access Surgery

Animals were anaesthetised with 3-5% Isoflurane using an anaesthetic vaporiser and induction chamber (Harvard Apparatus, UK) through 100% medical oxygen (flow rate 2 l/min). Mouse and rat surgery protocols followed recently a published protocol (Pacher, Nagayama et al. 2008).

The first step in the haemodynamic phenotyping required isolation of the right internal jugular vein (for antegrade catheterisation of right heart chambers) and right internal carotid artery (for retrograde aortic and left ventricular catheterisation) where necessary and is described as follows.

Measurement of Right Heart Pressures

Animals were placed on a heated pad (#TR200 Fine Science Tools Inc). Once the pedal reflex had been abolished a small incision in the neck was made to the right of the midline. With the use of a dissecting microscope and lateral blunt dissection the right external jugular vein (RJV) was identified. Curved forceps were used to free the vein with blunt dissection. The distal RJV was tightly tied off with 5-0 non-absorbable silk suture (Silkam®, B-Braun, Sheffield, UK) to halt venous return to the heart. Proximal to the insertion point of right subclavian vein a loose silk suture attached to a mosquito clip with traction was applied to the RJV. This left approx a 1 cm length of vein in which to insert our catheter. Under direct microscopic visualisation the vein was cleaned of any fatty tissues to enable successful cannulation of the true lumen of the vein. Using a 25G 5/8" orange needle with tip bent at 900 and the bevel pointing downwards the vein was punctured and the superior wall of the vein was immediately but gently lifted upwards to allow simultaneous insertion and advancement of the catheter. Catheters had been pre-soaked in saline for at least 30 min.

The appropriate catheter was advanced forwards and the proximal sling was tightened to avoid retrograde bleeding. Real time visualisation of pressure recording helped us to identify characteristic tracings for the right atrial and ventricular chambers. Once the catheter was stable within each chamber recordings were taken for subsequent analysis.

A recording of at least 10-20 heart beats was used to average the pressure measurements.

Right ventricular systolic pressure (RVSP), maximum and minimum derivatives of pressure (max and min dp/dt) were specifically recorded. RVSP served as a surrogate of pulmonary artery pressure as recordings of the latter were not possible with these straight tipped catheters. RVSP is identical to PASP in the absence of any obstruction at the level of the pulmonary valve. Once the catheter was removed the proximal RJV was tightly secured.

Measurement of Left Heart Pressures

Following completion of RVSP measurements the right carotid artery was identified, deep and lateral to the trachea. It was freed similar to the vein using curved forceps. A tight distal, loose mid and proximal segment ties (5-0 silk Suture) were applied. The latter was attached to a mosquito clip and traction applied. Using a similar technique for the vein, an arteriotomy was created and the catheter advanced into the aorta and left ventricle. Once pressure and volume tracings were stable and clear, the recordings were taken. An aortic pressure tracing by catheter pullback from the LV was recorded prior to removal of catheter. A recording of at least 10-20 heart beats was used to average the pressure measurements.

Harvesting and Processing of Tissue

Blood

Blood was allowed to coagulate on the bench and subsequently centrifuged at 1200 rpm for 15 min. The serum was collected, aliquoted, labeled and frozen at −80° C. until subsequent analyses. Tubes containing whole blood for RNA (PAXgene®, Qiagen/BD U.K or Tempus®, Applied Biosystems, UK) were frozen at −20° C. until subsequent isolation of RNA.

Lung Tissue

Protocol

After cardiac puncture the rodent was overdosed with anaesthetic followed by cervical dislocation. An incision in the upper abdominal wall was made to expose the liver. Whilst applying upward traction on the xiphoid process of the sternum, the diaphragm was carefully cut with fine scissors. The sternum and chest wall were resected away. The abdominal aorta was identified and cut (to exsanguinate). Using a 25 G orange needle and syringe the right ventricle was identified and flushed with PBS until the lungs became pale. The trachea was identified and freed between the medial clavicular borders. Whilst applying firm upward traction on the trachea, the heart and lungs were removed en-bloc from the posterior wall of thoracic cavity. Care was taken to avoid inadvertent lung puncture.

The right lung was secured tightly at the hilum using 5-0 silk sutures and separated away before being snap frozen in liquid nitrogen for subsequent isolation and determination of whole lung protein and RNA expression.

Polyethylene tubing was inserted into the trachea and secured tightly with a suture. The left lung was gently inflated manually with a syringe containing 10% phosphate buffered formalin (0.4% w/v $NaH_2PO_4.2(H_2O)$, 0.65% w/v $Na_2HPO_4.2(H_2O)$ and 4% v/v formaldehyde in water) and then both heart and left lung were fixed in formalin for 24 hours before transfer into PBS. From the rat prevention study onwards lungs were inflated using 20 cm $H_2O$ clamp set up to standardise inflation. The left lung was separated from the heart for subsequent histology.

Heart Weights and Right Ventricle Hypertrophy (RVH)

RVH was defined as the weight of the RV divided by the weight of the left ventricle/septum (RV/LV+S) as first described by Fulton et al.

Protocol

Using a small pair of fine scissors surrounding fat, tissue and great vessels were removed from around the heart. The atria were excised, cleared of any thrombus and weighed. The right ventricle was separated from the left ventricle and septum by the use of anatomical landmarks.

Starting from the right ventricular outflow tract (RVOT) the septal margin of the RV was dissected away to ensure no ridges of tissue were left. An incision was also made from the RVOT adjacent to and encircling the aortic root towards the medial tricuspid valve annulus to separate the base of the RV. From the lateral tricuspid annulus the RV free wall was cut away ensuring again no ridges of RV tissue remained. The incision continued towards the apex and back up-towards the RVOT.

Finally the left ventricle was cut and any clot removed from it before all chambers were padded dry and weighed.

Lung Histology and Immunohistochemistry

Tissue Processing and Histology

The left lung was divided in the sagital (rats) or transverse (mice) plane. Lungs were processed by first dehydrating them in graded alcohols (50% up to 100%). They were then placed in xylene before being embedded in molten paraffin wax. 5 μm thick paraffin embedded sections were cut and mounted onto slides for subsequent histology, immunohistochemical staining and morphometric analyses.

All slides were initially dewaxed by placing in xylene for 10 mins and then again for 2 mins. Slides were then rehydrated in graded alcohols (1 min in each of 100%, 100%, 90%, 70%, 50% and then finally water). Following any staining as a final common step, all slides were dehydrated in an identical but reverse order and mounted in DPX (Dibutyl Phthalate Xylene) and allowed to dry overnight.

Alcian Blue Elastic Van Gieson (ABEVG)

Dewaxed and rehydrated slides were oxidised in 0.25% potassium permanganate for 3 min and rinsed in distilled water before being bleached with 1% Oxalic acid for 3 min. Following rinsing, slides were stained with Carazzi's Haematoxylin for 2 min and differentiated in acid alcohol (1% v/v HCl in 70% IMS) for a few seconds prior to being submerged in hot running tap water for 5 min. Slides were then stained with Alcian Blue (1% w/v in 3% aqueous acetic acid, pH2.5) for 5 min. Slides were rinsed again with water and soaked rapidly in 95% IMS before being dipped into Miller's elastin stain for 30 min. Slides were then rinsed, placed in 95% IMS for a few seconds and rinsed in water again. They were then stained with Curtis' modified Van Gieson reagent for 6 min. Slides were then dehydrated in identical but reverse order to those for rehydration above before mounting in DPX.

Immunohistochemistry

Paraffin embedded 5 μm lung sections underwent immunohistochemical staining α-SMA for vascular smooth muscle cells, vWF to localise endothelial cells and PCNA for proliferating cells. Immunostaining for OPG was performed to identify any expression within pulmonary vascular lesions. Levels of apoptosis were determined with a colorimetric assay to detect DNA fragmentation (FRAGEL®, Calbiochem, UK) as specified by the manufacturer's instructions. A positive control was generated with DNAse treatment of a control slide.

Protocol

Following dewaxing and rehydration of slides, endogenous tissue peroxidases were blocked by incubating slides in 3% (v/v) hydrogen peroxide for 10 mins before being rinsed in tap water. Antigen retrieval (Slide permeabilisation) was done by incubating slides in either:
a) citrate buffer, pH 6.0 preheated to 95° C. for 20 min. before cooling for 20 min at RT. Tissue was then permeabilised by incubation in 0.5% (v/v) tritonX100 for 10 mins at RT (IHC for OPG)
b) 0.1% (w/v) Trypsin/TBS, pH7.8, preheated to 37° C. for 10 mins before stopping reaction by immersing in water (IHC for vWF)
c) for SMA staining an antigen retrieval step was not performed Slides were then blocked (to prevent non specific binding of secondary antibody) in 1% (w/v) skimmed milk/PBS for 30 mins at RT. Milk was tipped off and excess blotted away. The relevant primary antibody diluted in PBS was added and incubated as follows:
a) Monoclonal mouse anti-human aSMA 1:150, (#m081, Dako) for 1 hour at RT
b) Polyclonal rabbit anti-human vWF 1:300 (#A0082, Dako) for 1 hour at RT.
c) Polyclonal rabbit anti-human OPG 1:100 (#ab73400, Abcam) overnight at 4° C.

Slides were washed in PBS three times for 5 mins before adding a species specific biotinylated secondary antibody (1:200 dilution in PBS) for 30 minutes at RT. Slides were washed again in PBS three times for 5 mins and an avidin biotinylated enzyme complex added (Vectastain ABC Kit, Vector laboratories Inc. CA, US). Following a further PBS washing step, diaminobenzidine (DAB) substrate was added for 5-10 min. After optimum development the colour reaction was stopped by washing slides in tap water. Slides were then counterstained with Carazzi's haematoxylin for 1 minute before a final wash in water. Slides were dehydrated as described and mounted with DPX mountant. Slides were allowed to dry overnight before being examined under light microscopy Morphometric Lung and Image Analysis The degree of pulmonary vascular remodelling was quantified in arterioles by two methods and categorised according to vessel size (20-50 μm, 50-100 μm and >100 μm) (Schermuly, Dony et al. 2005). Vessels were scored blind to the experimental status of rodents.

Medial to Cross Sectional Area (Media/CSA) Ratio

Medial area/CSA represented the proportion of the total vessel area was taken up by muscularisation of the medial layer, as determined from α-SMA stained slides. Six vessels of each size group were analysed at a 40× objective (18 vessels/section and 1 section/rodent). Cross Sectional Area was the total area defined by the outer vessel circumference with the media defined as the area between the internal and external elastic lamina of the vessel.

Percentage of Vessels Thickened

Percentage of vessels thickened was determined using slides stained with ABEVG. For each slide 3-4 random fields of view were sampled using a 10× Objective (100× mag). The number of vessels that were fully occluded, partly occluded and non-thickened per size group were counted and expressed as a percentage of the total number of vessels in each view.

Quantification of Vascular Proliferation and Apoptosis Levels

To determine the levels of proliferation within remodelled vessels, the number of PCNA positive stained nuclei were counted and expressed as a percentage of total nuclei within the vessel. Where relevant, nuclei in the adventitia or perivascular area were also counted when in direct extension from the vessel of interest. Six vessels of each size were scored from each section (one section/animal) at a 40× objective.

In an identical manner the percentage of apoptosis positive nuclei (as determined from a colorimetric assay for levels of DNA fragmentation) were quantified for six vessels of each size per lung section (one section/animal).

Slides were viewed with a light microscope (Nikon eclipse E600) connected to a digital camera (Nikon digital site DSRi1) and NIS basic elements software (Nikon Inc.)

Studying the Expression of RNA and Protein from Rodent Lung Tissues

Isolation and Purification from Protein and RNA from Lung Tissue

Lung segments frozen in liquid nitrogen were ground using a pestle and mortar containing liquid nitrogen to a fine powder and weighed. Precautions were taken to minimise contamination by RNAase. Total protein and RNA were isolated using a commercial RNA/Protein purification kit (Norgen Biotek, Ontario, Canada) according to the protocol supplied by the manufacturer. The purification kit employed a spin column chromatography technique and allowed elution of proteins and RNA from the same sample within 30 minutes. Note: Qiagen Kits for Murine/Rat Interventions Protocol Briefly lysis solution was added to the lung tissue and then ethanol added. This was loaded on to a spin-column. After centrifugation at 14000 rpm, all nucleic acids within the solution were bound by a resin whilst the proteins were removed in the flow through. The bound RNA was washed, spun again and then purified RNA was eluted. The concentration of RNA in the elution was determined using a spectrophotometer (NanoDrop®, Thermo Scientific) and frozen at −80° C.

Following pH adjustment the protein flow through was reloaded on to the original spin column, centrifuged, washed and eluted.

Finally protein concentrations were determined using a commercial assay (DCTM protein assay, BioRAD Life Sciences, UK) according to the protocol provided by the manufacturer. Briefly it is a colorimetric assay that utilises a reaction between the protein and an alkaline copper tartrate solution. This is followed by a reduction step using Folin reagent. Absorbance was read at 750 nm. The quantity of protein was determined from absorbance data generated from a protein standard curve (Albumin, BSA, Pierce, Thermo Scientific Fisher, UK.) Protein samples were stored at −80° C.

Western Immunoblotting

Protocol

Proteins were separated by SDS-Polyacrylamide gel electrophoresis using a commercial electrophoresis kit (NuPAGE® Kit, Invitrogen). All buffers and reagents were part of the NuPAGE range unless otherwise stated. A volume containing 35 µg of protein purified from the lungs of rats from the time course experiment, sample buffer and a reducing agent made to a final volume of 30 µl (in deionised water) was heated to 70° C. for 10 min. Samples and a pre-stained marker ladder were then loaded onto 10 well pre-cast SDS polyacrylamide gels (NuPAGE® 4-12% Bis-Tris Mini gels, Invitrogen). In addition a sample of mixed experimental lung tissue was also loaded onto every gel as an additional control to allow for subsequent quantitative analysis.

Immediately prior to placing the loaded gels into an electrophoresis cell (XCell SureLock® Mini cell, Invitrogen) that already contained SDS running buffer, 500 µl of antioxidant was added. The Gel was run at 200V for 35 min.

Gels were transferred onto a nitrocellulose membrane (membrane and blotting pads had been pre-soaked in the transfer buffer and air bubbles removed) in transfer buffer (containing antioxidant and 10% methanol v/v) and ran at 30V for 60 min. Ponceau S staining was used to confirm adequate transfer.

The membranes were then blocked for 1 h in 10 ml of PBS with 5% milk (w/v) and 0.1% Tween-20 (v/v) on a shaking platform. Blots were rinsed in PBS/0.1% tween-20 three times before adding the relevant primary antibody in 5% milk/PBS/0.1% tween-20 on a shaking platform overnight at 4° C. (Mouse anti-human TRAIL 1:50, Novo Castro Laboratories, Co Durham, UK and anti Mouse Beta Actin 1:2000, Santa Cruz, Calif., USA).

Blots were rinsed three times for 10 min. before adding an appropriate, species specific peroxidise labelled secondary antibody diluted in PBS (polyclonal goat Anti-mouse immunoglobulin/HRP 1:2000, #p0447, Dako, Ely, UK)

Following a further rinse step as described enhanced chemoluminescence was performed by adding 1 ml of a commercial assay on to the blots for 5 min in the dark (West Dura Super Signal, Thermo scientific Fisher). Blots were developed in a dark room using autoradiography film (Hyper-Film™ GE Amersham, UK) and developer/fixer solutions.

Blots were stripped (Reblot Plus Mild Chemicon solution, Millipore) and reprobed for actin as described above.

The developed blots were dried and the ladder marked. The quantity of TRAIL in the bands was determined by normalising to actin and control samples using the densitometry function on commercial software (Syngene SNAP software, Chemigenius2 bioimaging system, SynGene).

Quantitative Real Time Polymerase Chain Reaction

Reverse Transcription of RNA for First Strand Synthesis

This step was performed using components provided in a SuperScript™ III first strand synthesis system (Invitrogen™ Life technologies, UK). A volume containing 3 µg of total RNA isolated from the lungs (and whole blood using PAXgene tubes) of experimental rodents was made to 10 µl using molecular grade water. 1 µl of random hexamer primers (50 ng) and 1 µl of a 10 mM dNTP were added to this and heated to 65° C. for 5 minutes as a denature step. Samples were put on ice until 10 µl of a cDNA synthesis mix [containing 10×RT buffer (2 µl), 25 mM $MgCl_2$ (4 µl), 0.1M DTT (2 µl), RNase-OUT™ MA and SuperScript™ III reverse transcriptase (1 µl)] was added to this solution and mixed. Samples were heated in a thermal cycler (G Storm GS1, GRI Ltd, Essex, UK) with parameters set as follows i) 25° C. for 10 min (annealing step), ii) 50° C. for 50 min (cDNA synthesis) and finally iii) 85° C. for 5 min before being held at 4° C. (to terminate the reaction). 1 µl of RNaseH was added to each tube before a final incubation step at 37° C. for 20 min.

Alternatively (for all mouse and rat interventions) 2 µg of RNA was reverse transcribed using a commercial high capacity RNA to cDNA kit (Applied Biosystems). Briefly RNA was added to PCR tubes containing 10 µl of 2×RT buffer and 1 µl of an RT enzyme mix. Samples were heated in a thermal cycler (G Storm GS1, GRI Ltd, Essex, UK) with parameters set as follows i) 37° C. for 60 min ii) 95° C. for 5 min and then held at 4° C. to terminate the reaction.

Real Time Quantitative PCR-need to Get Numbers for Mouse

Amplification of the target lung cDNA derived from the RT step above was then next performed. A volume containing Song of each cDNA was diluted to a volume of 4.5 µl using sterile water. 5 µl of a TaqMan® gene expression master mix-2× (Applied Biosystems™ Life Technologies, UK) along with 0.5 µl of the relevant target gene primers (10×) were added to the cDNA in the relevant well of a 384-well plate. Target genes were tested are listed in table 1 (all from Applied Biosystems™) 18s and ATP5B were selected as endogenous control genes having been determined in prior testing (GeNORM assay). Samples (in duplicate) for each gene were loaded on the same plate. The plate was centrifuged at 1000 rpm for 1 min and the reaction was run on a 7900HT fast real time PCR system (Applied Biosystems™). Relative expression for each gene was quantified by comparing the test gene with the housekeeping control gene and comparing this ratio between an experimental and control subject (delta, delta CT method) for each gene using SDS software (v2.2.1, Applied Biosystems™).

Applied Biosystems—Assay ID's for gene expression analyses.

| Gene | Rat primers | Mouse primers |
|---|---|---|
| ATP5B | Rn01756316 | Mm00443967-g1 |
| 18s | Hs03003631-m1 | Hs03003631-m1 |
| TRAIL | Rn00595556-m1 | Mm00437174-m1 |
| OPG | Rn00563499-m1 | Mm00435452-m1 |
| BMPR2 | Rn01437210-m1 | Mm03023976-m1 |
| CCL5 | Rn00579590-m1 | Mm1302428-m1 |
| IL1R1 | Rn00565482-m1 | Mm00434237-m1 |
| IL1R2 | Rn00588589_m1 | Mm00439622-m1 |

Statistical Analysis

Data were plotted and analysed using Prism® v5.0 (Graphpad, US) software. Data are expressed as Mean [standard error] unless indicated otherwise. Two groups were compared with Student's unpaired t-test and three or more groups by ANOVA with Bonferroni post comparison testing (where indicated). Statistical significance was defined by a p value of ≤0.05.

EXAMPLE 1

Figure 1B:
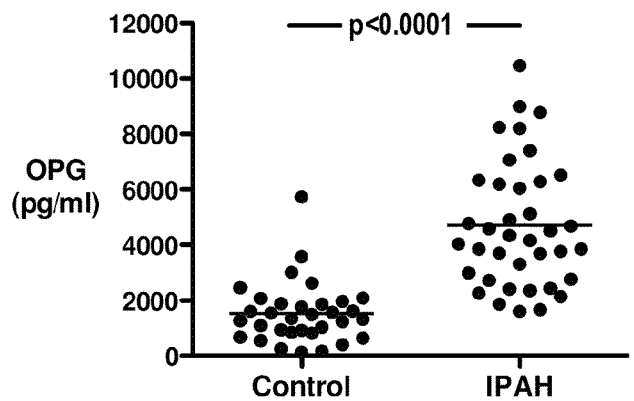
Figure 1C:
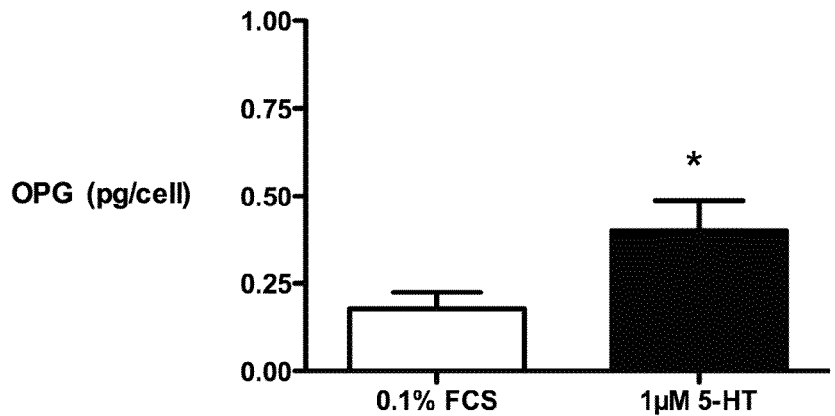
Figure 1D:
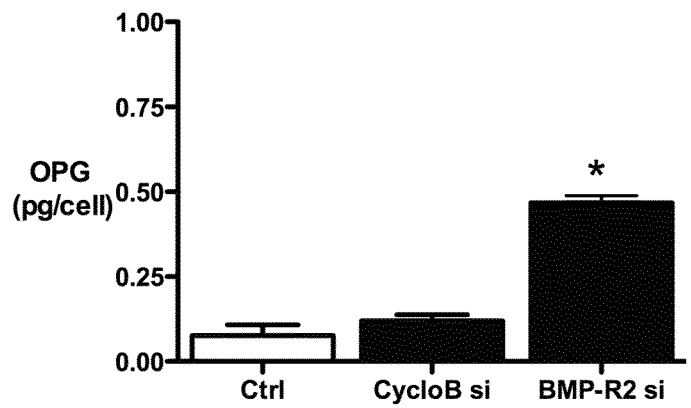
Figure 1E:
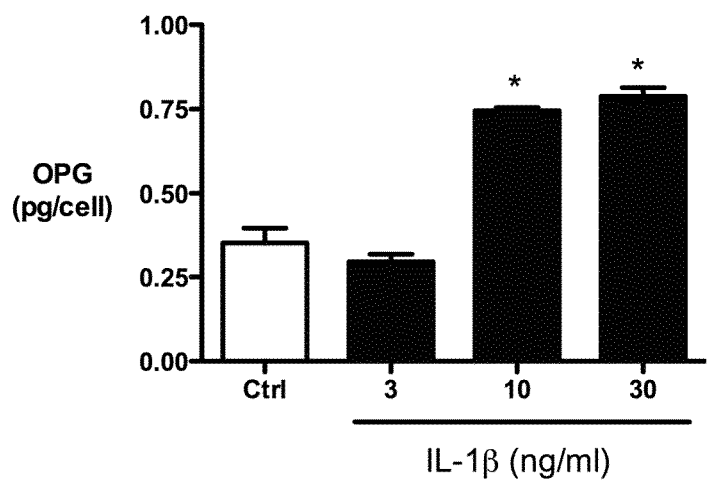

OPG Expression is Increased in PAH:

Using mRNA isolated from pulmonary artery smooth muscle cells (PASMC) explanted and grown in vitro from transplanted lungs of patients with idiopathic pulmonary arterial hypertension, we have demonstrated that OPG gene expression (FIG. 1A), and serum levels of protein (FIG. 1B) are increased compared to those isolated from control samples.

EXAMPLE 2

Multiple Pathways Associated with PAH Pathogenesis Increase OPG Secretion from PASMCs:

The addition of serotonin (5-Hydroxytriptamine, 5-HT) (Sigma) (A), the knock-down of bone morphogenetic protein receptor type 2 (BMP-R2 siRNA, Dharmacon) (B) or the addition of interleukin-1 beta (IL-1b, R&D Systems) (C) to human PASMC results in a significant increases in OPG secretion.

EXAMPLE 3

Figure 1F:
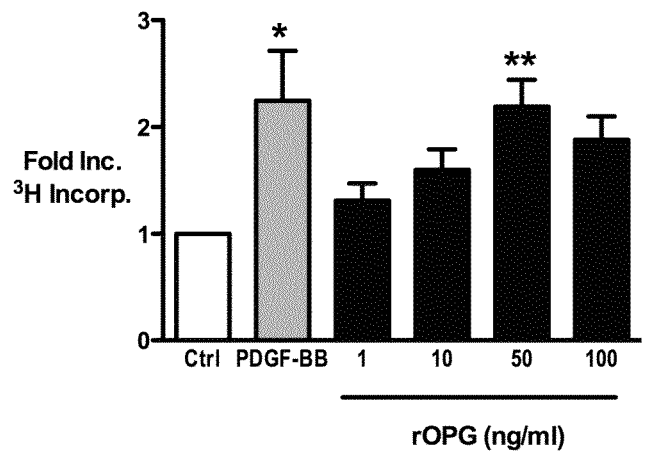
Figure 1G:
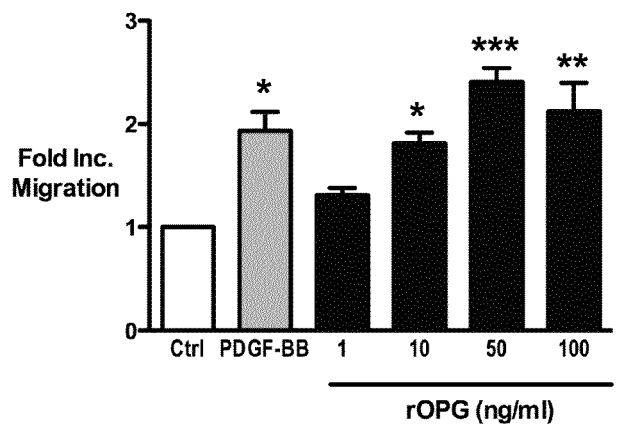

OPG Induces the Proliferation and Migration of PASMC:

The addition of recombinant human OPG (R&D Systems) to human PASMC results in a dose-dependent increase in proliferation (FIG. 1F) and migration (FIG. 1G).

EXAMPLE 4

Figure 1H:
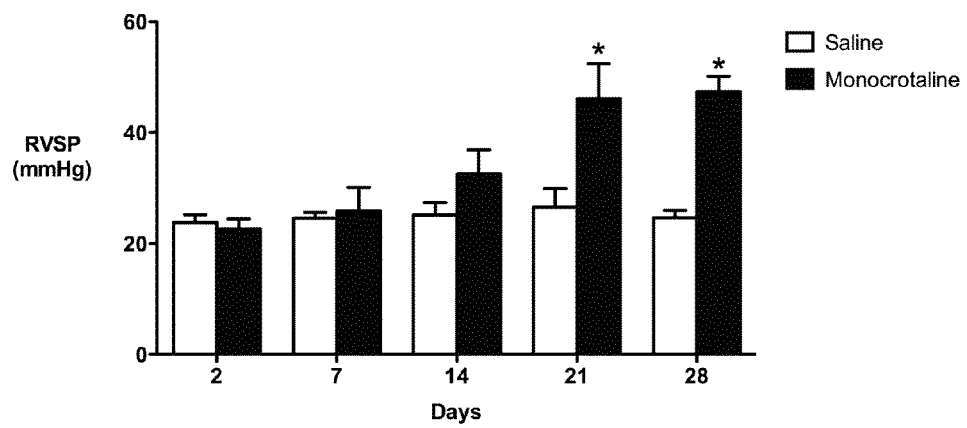
Figure 1I:
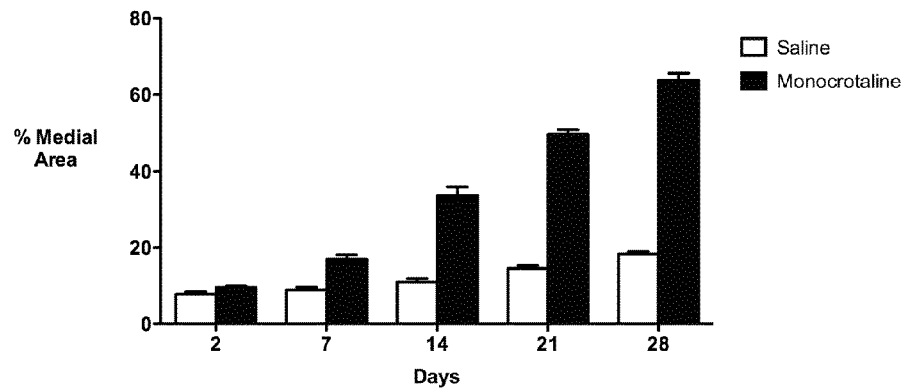
Figure 1J:
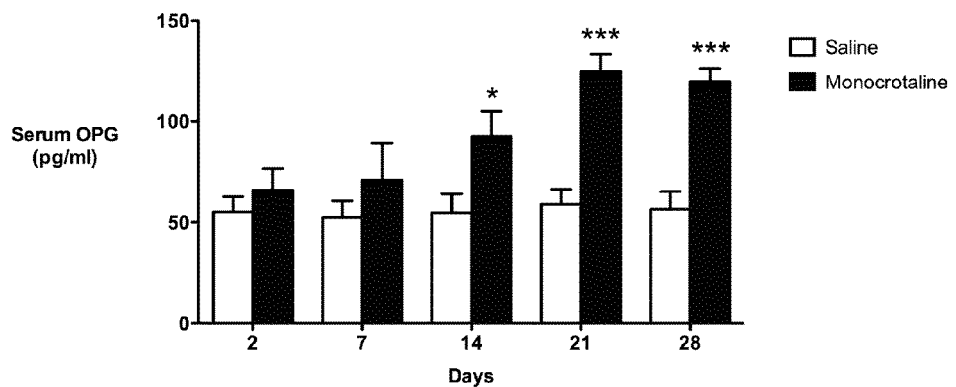
Figure 1K:
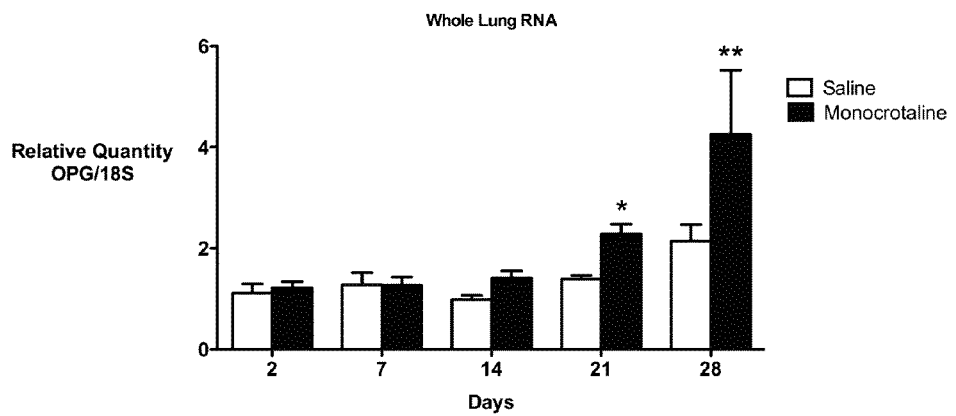
Figure 1L:
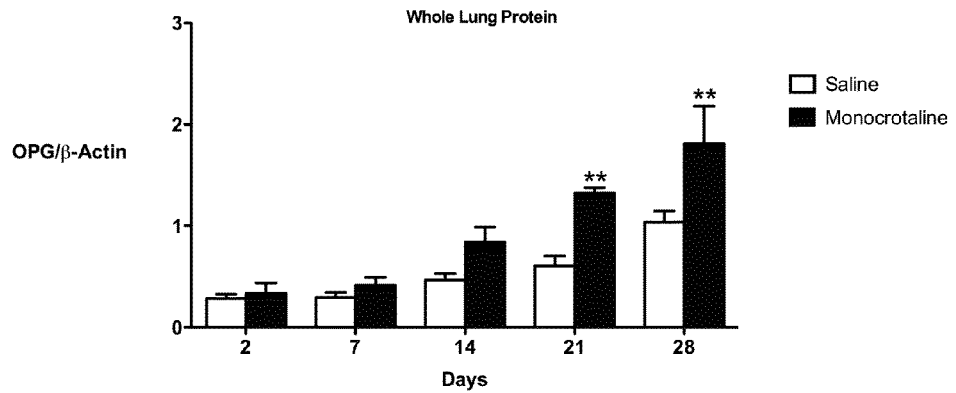

OPG Expression Increases with Disease Progression in the Rat Monocrotaline Model of PAH:

Seven rats per group, per time point were injected with either 60 mg/ml of monocrotaline or saline as a control. Rats underwent cardiac catheterization prior to sacrifice and harvest of heart and lung tissue at 2, 7, 14, 21 and 28 days post disease initiation. As per previously published data haemodynamic rises consistent with the disease process were observed from day 14 with significant increases observed at day 21 and 28 (FIG. 1H & FIG. 1I). ELISA performed on rat serum revealed that significant elevations in OPG were detected from as early as day 7 and prior to haemodynamic alterations in the Mct-treated rats (FIG. 1J), TaqMan PCR analysis of whole lung RNA revealed a significant increase in OPG gene expression from day 21 in the Mct-treated rats (FIG. 1K). Western analysis of whole lung protein isolated from the rats was probed with an anti-OPG antibody. The blots were semi-quantitatively analysed for OPG expression, normalized to beta-actin. Significant increases in OPG protein was detected from day 21 in the monocrotaline treated rats compared to saline controls (FIG. 1L).

EXAMPLE 5

Figure 1M:
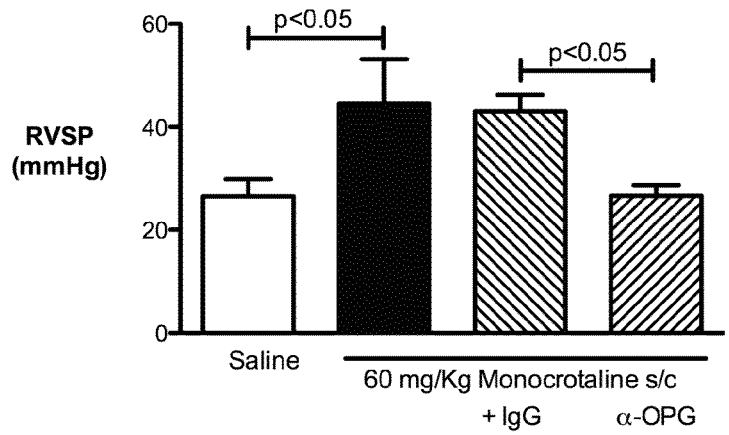
Figure 1N:
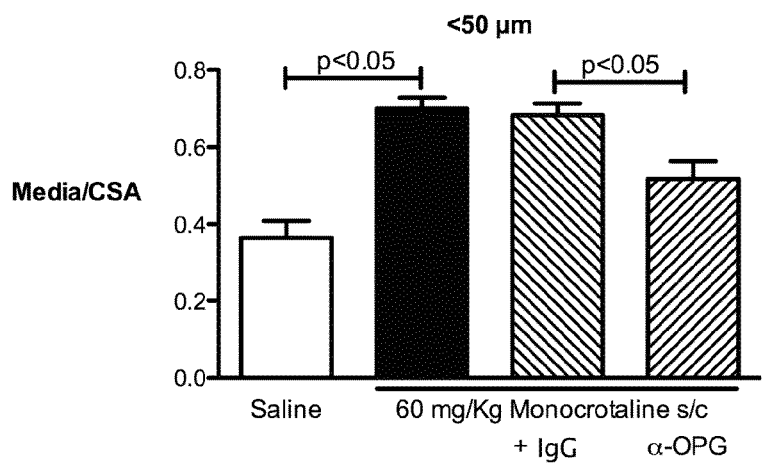
Figure 1O:
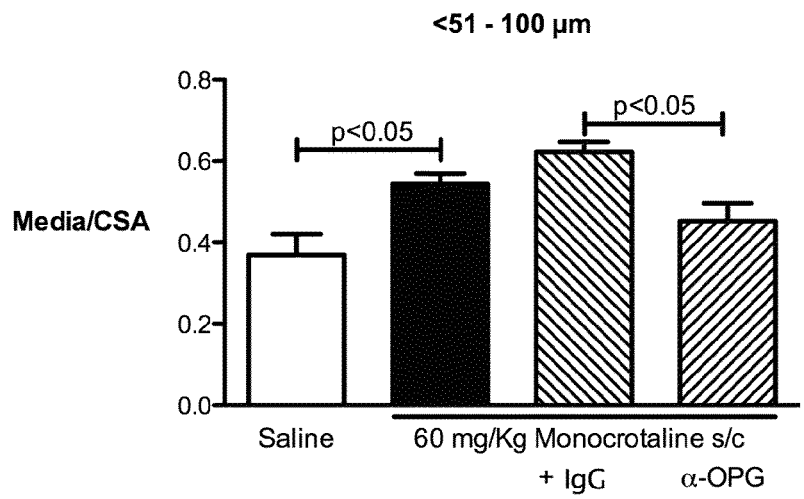

Anti-OPG Antibody Treatment Prevents the Development of PAH in the Monocrotaline Rat Model:

Four rats per group were implanted with an osmotic mini pump to deliver either an anti-OPG antibody or IgG as control, at the same time as receiving a 60 mg/kg dose of monocrotaline. After 21 days the rats underwent cardiac catheterization prior to sacrifice and harvest of heart and lung tissue as above. The rats receiving the anti-OPG antibody showed a significant reduction in RVSP compared to the rats receiving IgG (FIG. 1M). The reduction in RVSP was also associated with a significant reduction in pulmonary vascular remodelling (media/CSA) of the small pulmonary arteries/arteriole (<50 μm, FIG. 1N) and small to mid-sized pulmonary arteries (51-100 μm, FIG. 1O).

EXAMPLE 6

Figure 1P:
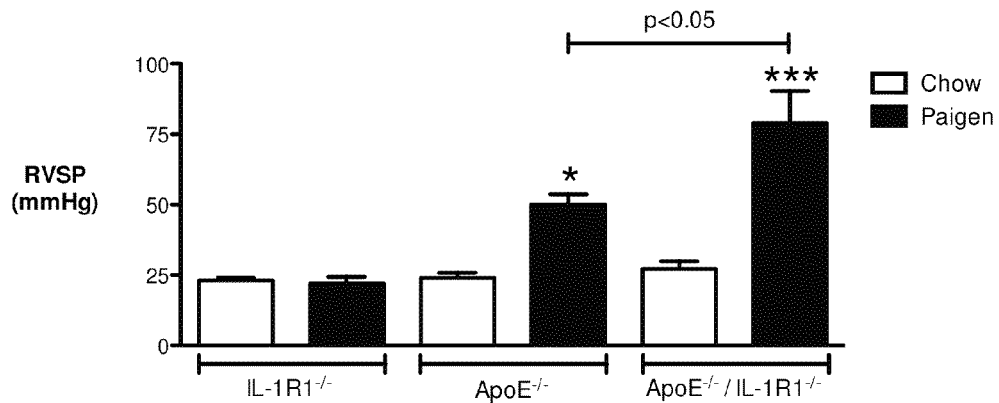
Figure 1Q:
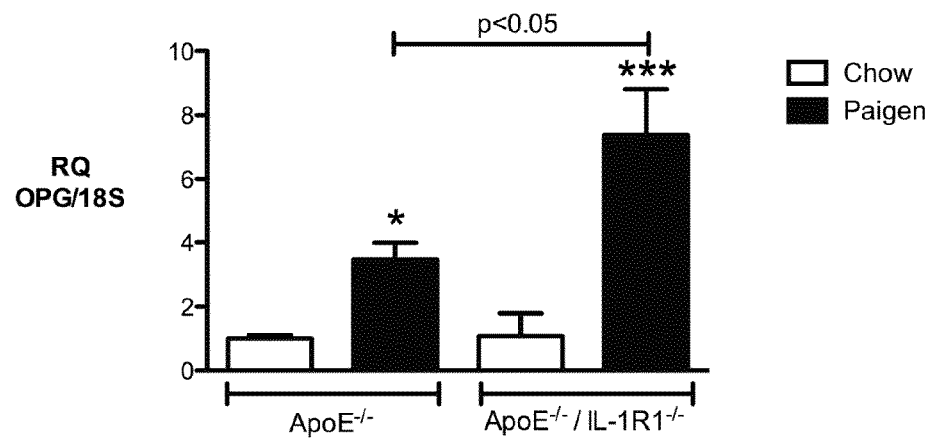
Figure 1R:
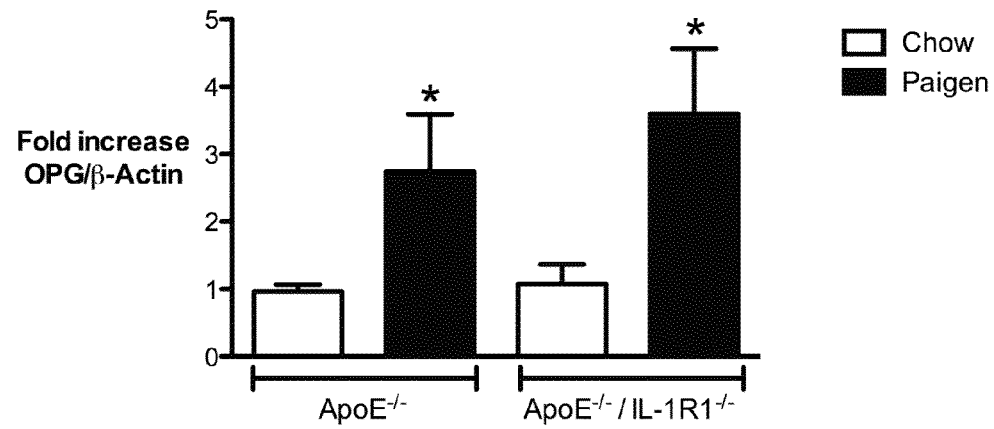
Figure 1S:
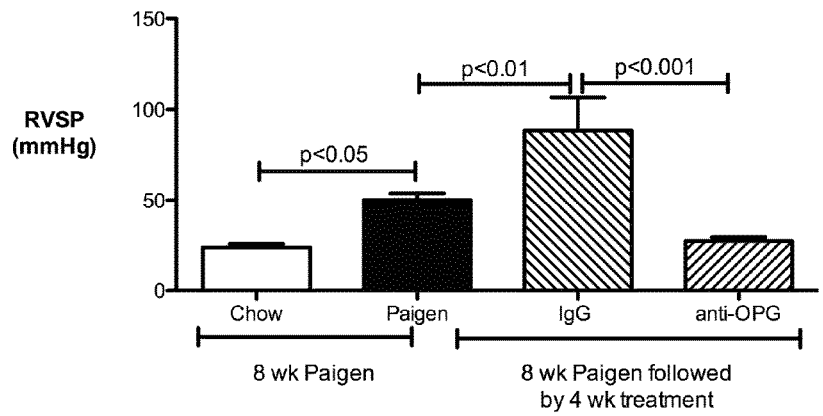
Figure 1T:
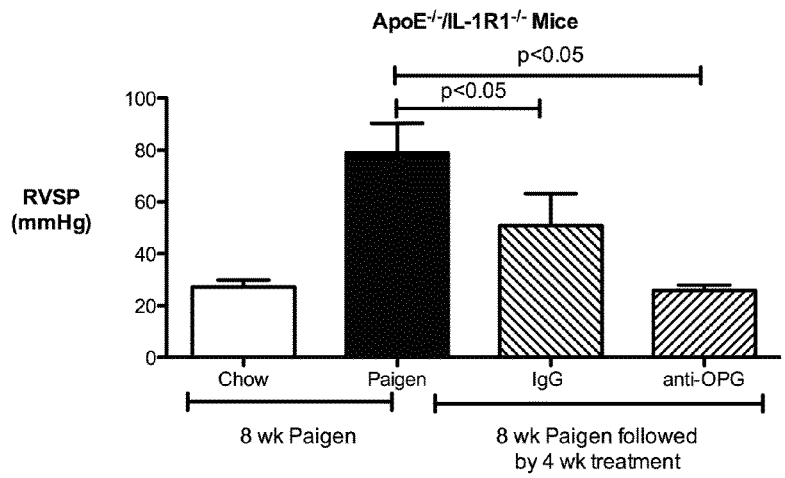
Figure 1U:
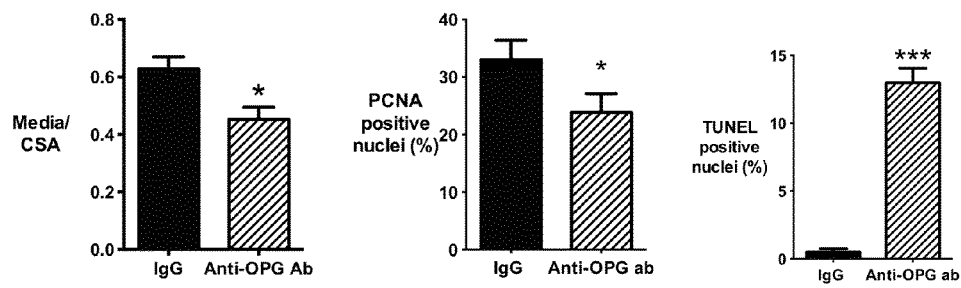
Figure 1V:
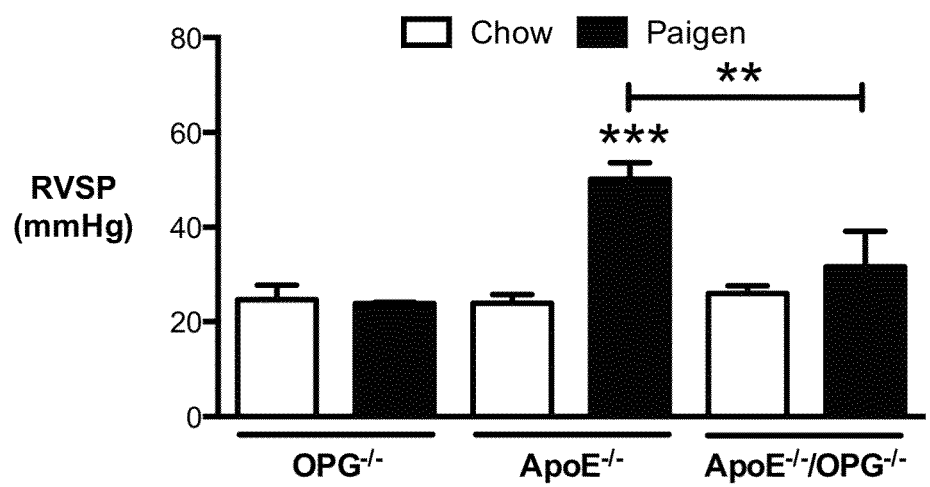

OPG Expression is Increased in the Paigen Diet-Fed ApoE$^{-/-}$ Mouse Model:

ApoE$^{-/-}$ or ApoE$^{-/-}$/IL-1R1$^{-/-}$ mice fed the Paigen diet for 8 weeks developed significant increases RVSP (FIG. 1P). TaqMan PCR analysis of whole lung RNA revealed a significant increase in OPG gene expression in the Paigen fed mice (FIG. 1Q). Western analysis of whole lung protein isolated from the mice was probed with an anti-OPG antibody. The blots were semi-quantitatively analysed for OPG expression, normalized to beta-actin. Significant increases in OPG protein was detected in the Paigen fed mice (FIG. 1R).

EXAMPLE 7

Treatment of Established PAH with an Anti-OG Antibody Induces Disease Reversal:

ApoE$^{-/-}$ (figure S) or ApoE$^{-/-}$/IL-1R1$^{-/-}$ (figure T) mice after 8 weeks of feeding on the Paigen diet were implanted with osmotic pumps delivering either anti-OPG antibody of IgG for 4 weeks. Mice that received the anti-OPG antibody displayed a significant reduction in RVSP compared to IgG treated mice, to near normal levels.

EXAMPLE 8

OPG is a secreted molecule that interacts with Tumor Necrosis Factor-Related Apoptosis-Inducing Ligand (TRAIL). We hypothesised that circulating levels of OPG and TRAIL would provide a much-needed biomarker for PAH. The levels of OPG and TRAIL were measured in serum obtained from patients with IPAH, chronic thromboembolic pulmonary hypertension (CTEPH) (pre- & post-endarterectomy), acute coronary syndrome, stable angina and appropriate controls under ethical approval from both Sheffield Teaching Hospitals and Papworth Hospital Foundation Trusts, UK. Levels of OPG, TRAIL and the OPG/TRAIL ratio were then compared with clinical assessments. OPG expression was significantly increased, and TRAIL was significantly decreased in serum from patients with IPAH compared to all other groups (P<0.0001, n=37-76). IPAH patients had significantly higher OPG/TRAIL than either control, or other disease groups, which correlated with Cardiac Index (p<0.0001, R=0.62) and Right Atrial Pressure (p<0.05, R=0.43) but not mean pulmonary artery pressure or 6 minute walk test. OPG was significantly lower in CTEPH patients at 3 months following endarterectomy but there was no significant difference in the levels of TRAIL. Based upon these data, the OPG/TRAIL ratio may be a useful new biomarker for tracking PAH pathogenesis. Combining the two molecules may provide greater power to distinguish PAH pathogenesis. Further work is clearly required to consider other associated PAH groups, and effect of treatments in a larger cohort of patients.

The invention claimed is:

1. A method for treating and reversing the symptoms of pulmonary hypertension in a subject, comprising:
    administering to the subject having pulmonary hypertension an effective amount of an antagonistic antibody, or an active antigen binding antibody fragment thereof, that binds to an amino acid sequence having at least 95% sequence identity to the amino acid sequence shown in SEQ ID NO: 1 and inhibits osteoprotegerin (OPG) protein activity, thereby treating and reversing the symptoms of pulmonary hypertension in the subject.

2. The method according to claim 1, wherein said antagonistic antibody is a polyclonal antibody.

3. The method according to claim 1, wherein said antagonistic antibody is a monoclonal antibody.

4. The method according to claim 1, wherein said active antigen binding antibody fragment is selected from the group consisting of: Fab, Fab$_2$, F(ab')$_2$, Fv, Fc, Fd, and single chain antibody fragment.

5. The method according to claim 1, wherein said antagonistic antibody is a chimeric antibody.

6. The method according to claim 1, wherein said antagonistic antibody is a humanized or human antibody.

7. The method according to claim 1, wherein said antagonistic antibody or active antigen binding antibody fragment binds the ligand binding domain of OPG.

8. The method according to claim 1, further comprising administering to the subject an effective amount of at least one additional agent effective in the treatment of pulmonary hypertension.

9. The method according to claim 8, wherein said additional agent is selected from the group: calcium channel blockers, diuretics, endothelin receptor antagonists, prostacyclins, soluble guanalate cyclase and phosphodiesterase inhibitors.

10. The method according to claim 1, wherein the pulmonary hypertension is selected from the group consisting of: pulmonary arterial hypertension and PH associated with lung disease.

11. The method of claim 1, wherein the subject is a human subject.

* * * * *

SEQUENCE LISTING

```
<160> NUMBER OF SEQ ID NOS: 2

<210> SEQ ID NO 1
<211> LENGTH: 401
<212> TYPE: PRT
<213> ORGANISM: Homo sapiens

<400> SEQUENCE: 1

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320
```

```
Pro Ser Asp Gln Ile Leu Lys Leu Leu Ser Leu Trp Arg Ile Lys Asn
            325                 330                 335

Gly Asp Gln Asp Thr Leu Lys Gly Leu Met His Ala Leu Lys His Ser
        340                 345                 350

Lys Thr Tyr His Phe Pro Lys Thr Val Thr Gln Ser Leu Lys Lys Thr
            355                 360                 365

Ile Arg Phe Leu His Ser Phe Thr Met Tyr Lys Leu Tyr Gln Lys Leu
        370                 375                 380

Phe Leu Glu Met Ile Gly Asn Gln Val Gln Ser Val Lys Ile Ser Cys
385                 390                 395                 400

Leu

<210> SEQ ID NO 2
<211> LENGTH: 1206
<212> TYPE: DNA
<213> ORGANISM: Homo sapiens

<400> SEQUENCE: 2
atgaacaact tgctgtgctg cgcgctcgtg tttctggaca tctccattaa gtggaccacc      60
caggaaacgt tcctccaaa gtaccttcat tatgacgaag aaacctctca tcagctgttg      120
tgtgacaaat gtcctcctgg tacctaccta aaacaacact gtacagcaaa gtggaagacc     180
gtgtgcgccc cttgccctga ccactactac acagacagct ggcacaccag tgacgagtgt    240
ctatactgca gccccgtgtg caaggagctg cagtacgtca agcaggagtg caatcgcacc   300
cacaaccgcg tgtgcgaatg caaggaaggg cgctaccttg agatagagtt ctgcttgaaa    360
cataggagct gccctcctgg atttggagtg gtgcaagctg aaccccaga gcgaaataca     420 gtttgcaaaa gatgtccaga tgggttcttc tcaaatgaga cgtcatctaa agcaccctgt    480
agaaaacaca caaattgcag tgtctttggt ctcctgctaa ctcagaaagg aaatgcaaca    540
cacgacaaca tatgttccgg aaacagtgaa tcaactcaaa atgtggaat agatgttacc     600 ctgtgtgagg aggcattctt caggtttgct gttcctacaa agtttacgcc taactggctt    660
agtgtcttgg tagacaattt gcctggcacc aaagtaaacg cagagagtgt agagaggata    720
aaacggcaac acagctcaca gaacagact tccagctgc tgaagttatg gaaacatcaa     780
aacaaagacc aagatatagt caagaagatc atccaagata ttgacctctg tgaaaacagc    840
gtgcagcggc acattggaca tgctaacctc accttcgagc agcttcgtag cttgatggaa   900
agcttaccgg gaagaaagt gggagcagaa gacattgaaa aacaataaa ggcatgcaaa     960 cccagtgacc agatcctgaa gctgctcagt tgtggcgaa taaaaatgg cgaccaagac   1020 accttgaagg gcctaatgca cgcactaaag cactcaaaga cgtaccactt tcccaaaact   1080
gtcactcaga gtctaaagaa gaccatcagg ttccttcaca gcttcacaat gtacaaattg   1140
tatcagaagt tattttaga aatgataggt aaccaggtcc aatcagtaaa ataagctgc   1200 ttataa                                                            1206
```